United States Patent [19]
Appino et al.

[11] Patent Number: 5,582,815
[45] Date of Patent: Dec. 10, 1996

[54] DEVICE FOR DISPENSING A THERAPEUTIC OR COSMETIC SUBSTANCE, THE INERT VEHICLE OF WHICH IS A VOLATILE POLYDIORGANOSILOXANE, AND COMPOSITION INTENDED TO BE USED IN THE DEVICE

[75] Inventors: Jim Appino, Doylestown, Pa.; Jean-Marc Aiache, Clermont-Ferrand, France

[73] Assignee: Laboratoires CILAG, Levallois-Perret, France

[21] Appl. No.: 291,434

[22] Filed: Aug. 16, 1994

[30] Foreign Application Priority Data

Aug. 18, 1993 [FR] France ................. 93 10075

[51] Int. Cl.$^6$ ............................................. A61K 9/14
[52] U.S. Cl. ................................. 424/45; 424/46
[58] Field of Search ......................... 424/45, 46, 43

[56] References Cited

U.S. PATENT DOCUMENTS 5,292,530  3/1994  McCrea et al. ........................ 424/66

FOREIGN PATENT DOCUMENTS

| 0229640 | 1/1987 | European Pat. Off. . |
| 0468564 | 4/1991 | European Pat. Off. . |
| 0478456 | 9/1991 | European Pat. Off. . |
| 3330447 | 3/1985 | Germany . |
| 3810730 | 10/1989 | Germany . |

OTHER PUBLICATIONS

Josef Roidl; Zeitschrift fur die Korperpflegemittel–, Parfumerie–, Riechstoff–u Aerosol–Industrie; Kosmetika Aerosole Riechstoffe; Nov. 12, 1987; pp. 685–689.

Primary Examiner—Nathan M. Nutter
Attorney, Agent, or Firm—Jacobson, Price, Holman & Stern

[57] ABSTRACT

The present invention relates to a device enabling a therapeutic or cosmetic substance to be dispensed in the form of aerosol particles.

The device according to the invention is of the two-compartment type or has a pump body mounted on it and has the characteristic feature that it contains a composition including an active substance and an inert vehicle which is one or more polydiorganosiloxanes of sufficient volatility to ensure expulsion of the composition in the form of aerosol particles.

The invention also relates to the composition intended to be used in the device.

18 Claims, 1 Drawing Sheet

5,582,815

DEVICE FOR DISPENSING A THERAPEUTIC OR COSMETIC SUBSTANCE, THE INERT VEHICLE OF WHICH IS A VOLATILE POLYDIORGANOSILOXANE, AND COMPOSITION INTENDED TO BE USED IN THE DEVICE

The present invention relates to a device which enables a therapeutic or a cosmetic substance to be dispensed in the form of aerosol particles.

It also relates to a sprayable composition which is intended in particular to be used in the device according to the invention, and a cosmetic treatment method.

Aerosol sprays which enable various substances, in particular for cosmetic or therapeutic use, to be dispensed and which comprise fluorocarbon gases (CFC's or HFA's) as propellant gases are being progressively banned on account of the harmful effects of said gases on the atmosphere.

In order to replace fluorocarbon propellent gases, various devices involving, on the one hand, a propellent gas (non-flurocarbon) and, on the other hand, an inert vehicle which allows the active substance to be accompanied to its site of application, have been proposed.

Some of these devices, known commonly as two-compartment devices, are formed of a rigid outer container and an elastic inner container, the upper edge of which is attached to the outer container. A valve-carrying lid, placed on the upper edge of the outer container, and a flow valve which extends into the inner container are mounted on the outer container, a propellent gas being placed in the free space separating the outer container from the inner container.

When the flow valve is actuated, the propellent gas forces the product contained in the inner container outwards via the flow valve which is then opened.

These devices are described in particular in Patent Applications FR-A-2 436 085 and FR-A-2 663 909.

Other devices consist of a rigid container on which is mounted a pump body comprising a variable-volume pump chamber, on the inside of which is housed a piston, with an inlet hole in order to establish a filling communication for the cheer with the container and an outlet hole to allow external emission of the active substance. In this case, the propellent gas is provided by the compression of a fluid, which is most often air, on the inside of the container by means of the actuation of the pump chamber piston.

These devices are described in particular in Patent Applications FR-A-2 647 418 and FR-A-2 643 338.

However, the inert vehicles contained in the containers, mixed with the active substance, exhibit certain disadvantages associated with their inherent chemical nature, which makes the operation of such devices not very satisfactory.

This is the case in particular for the inert vehicles based on ethyl alcohol.

Moreover, it is known in cosmetics or in medicine to use solutions, gels or sticks containing polydiorganosiloxanes as active substance promoting spreading, for topical applications.

U.S. Pat. No. 4,346,079 proposes an anti-perspirant composition containing a gelified alcoholic solution of an anti-perspirant compound, the gelling agent comprising fatty acid salts such as sodium stearate and a small amount of a siloxane, the viscosity of which is between 0.01 and 25 centistokes, such as polydimethylsiloxanes, polyphenylmethylsiloxanes and cyclic polydimethylsiloxanes.

Moreover, European Patent Application EP-A-0 211 555 describes a transparent silicone composition containing a small amount of a liquid fatty alcohol or of a liquid polyoxyalkylated alcohol. Among the silicones used, the document cites linear or cyclic polymethylsiloxanes having one to six methylsiloxane units. These compositions find an application in cosmetics (shampoos, deodorants, anti-perspirants, lotions and perfumes). In other terms, the volatile silicones in these preparations are vehicles which ensure a good spreading of the active substance and/or a good penetration of the latter when the composition has already been deposited on the support to be treated.

It was unexpectedly found that the polydiorganosiloxanes of sufficient volatility could be used as inert vehicles for the dispensing devices in the form of an aerosol of a therapeutic or cosmetic active substance.

The object of the present invention is thus to propose a new device containing such an inert vehicle and allowing a totally satisfactory application of the active substance to the skin.

According to the invention, the term inert vehicle is employed to denote the dispersion medium which will bring the active substance from the inside of the reservoir to the support to be treated.

This is thus a separate function from that consisting in facilitating the spreading on the skin of a composition which has already been deposited thereon by a suitable means.

Moreover, it has unexpectedly been observed that the deposition thus obtained by the use of the device was of great homogeneity and great regularity, while at the same time providing a pleasant feel compared with similar deposits produced by other means.

The invention thus relates to a device which enables a therapeutic-or cosmetic active substance to be dispensed in the form of an aerosol, consisting of a container containing a composition including the active substance and an inert vehicle, a flow valve extending into said container and a means of propulsion, wherein the inert vehicle is one or more polydiorganosiloxanes of sufficient volatility to ensure the expulsion of the composition in the form of an aerosol when the flow valve is opened.

Figure 1:
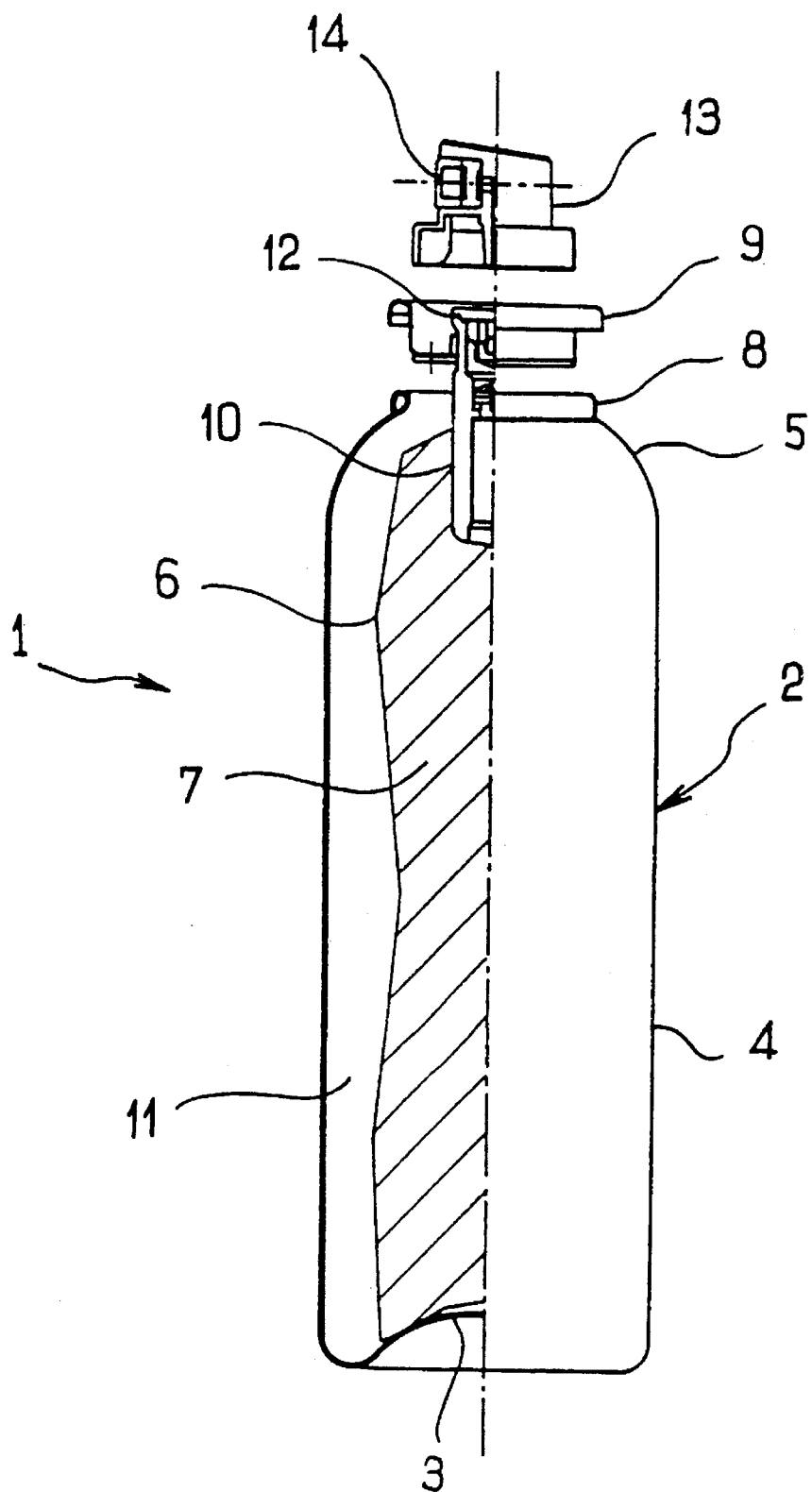
FIG. 1 is a half-section side view of a spray device in accordance with the present invention.

The devices which are used within the context of the present invention may contain, on the one hand, a propellent gas and, on the other hand, an inert vehicle. These devices may be of the two-compartment type or of the variable-volume pump chamber type.

In a known manner, the two-compartment devices are formed of an elastic inner container containing the composition and a rigid outer container, the free space separating the outer container from the inner container being occupied by a propellent gas. The variable-volume pump chamber devices are formed of a rigid container containing the composition, combined with a pump chamber communicating with said container.

They may also be of the type in which the pump piston which is in the chamber, actuated by the push button, allows the composition to be expelled without requiring the action of propellent gases. These devices are particularly preferred, and one example of such a device is that marketed by the company Valois (France) under the designation VP3 pumps.

Polydiorganosiloxane of sufficient volatility is understood to refer to compounds or a mixture of compounds having a vapour pressure of the order of 3.8 kPa as against 2.3 kPa for water and a heat of evaporation of the order of 192.5 J/g as against 2256 J/g for water. Among these polydiorganosiloxanes, there may be mentioned cyclic polydimethylsiloxanes of formula $(Me_2SiO)x$ in which x is an integer equal to 3 or 4, and linear polydimethylsiloxanes terminated by methyls, of formula $Me(Me_2SiO)ySiMe_3$, in which y is an integer equal to 1, 2 or 3.

Within the context of the device according to the invention, the polydiorganosiloxane compound used as inert vehicle will preferably be hexamethyldisiloxane.

This compound is manufacturered for example by the company DOW-CORNING and carries the reference Q7-9179 or by PHONE-POULENC reference Silbione Oil 70041 V 0,65. The physico-chemical properties of this product are in particular described in the sales catalogues edited by these companies. These compounds are moreover known for their compatibility with a use in cosmetics or in dermatology in topical form.

These compounds preferably have a purity which is greater than or equal to, preferably greater than, 99% or advantageously 99.2% and pass through a 400 mesh sieve.

The inert vehicle and the active substance form a thixotropic mixture, that is to say that it is in gel form at rest, whereas the application of a downwards movement in particular allows it to be reconverted into liquid ready to be expelled under the action of the propellent gas.

In order to improve the thixotropic nature of the mixture, it is advantageous to add to the compositon containing the inert vehicle an agent which is known to improve the thixotropy. This agent will in particular be based on collsidal silica, for instance the compound known under the trade name Aerosil® (marketed by the company DEGUSSA).

Moreover, the composition will advantageously comprise densifying fillers, in particular based on silica, for instance talc and additives improving the presentation, in particular the smell of the mixture, for instance fragrances.

The composition will either be in solution form when the active substance is soluble in the inert vehicle or in suspension form in the case of insolubility of the active substance in the inert vehicle.

Thus, the active substance transported in disperse form by the vehicle may either be in liquid form or in solid form.

The active substance will preferably be transported in powder form and the compounds forming the active substance will consequently be chosen from those which form a suspension in the inert vehicle.

Among these compounds, it is advantageous to use as active substance an antifungal agent, for instance imidazoles or triazoles, in particular one which is based on econazole. Of course, other antifungal agents may also be used within the context of the present invention.

As other active substances which may advantageously be used within the context of the invention, there may in particular be mentioned the following cosmetic products: "skin antiseptics, anti-perspirants, deodorants, and pharmaceutical products chosen from haemostatic agents, antibiotics, protective polymers, cicatrizing agents, hormones and substances absorbed by the skin which are capable of a general activity (cardiotonic agents and the like)".

According to a preferred variant, the sprayable composition consists in percentage by weight of:
75 to 95% of hexamethyldisiloxane,
0.01 to 15% of therapeutic or cosmetic substance,
0 to 10% of agent improving the thixotropy, preferably at least 1%, and
0 to 20% of fillers or additives, preferably at least 5%.

The sprayable composition preferably consists in percentage by weight of:
80 to 90% of hexamethyldisiloxane,
0.1 to 5% of therapeutic or cosmetic substance,
0 to 10% of agent improving the thixotropy, preferably at least 1%, and
0 to 20% of fillers or additives, preferably at least 5%.

By way of illustration of the present invention the single diagram attached as FIG. 1 illustrates a two-compartment device such as is known in the art, which may be suitable for use in the present invention.

The diagram represents a half-section along the longitudinal axis of such a device.

In accordance with this diagram, the disperser device 1 includes a rigid outer container body 2 consisting of a base 3 from which there extends vertically upwards a peripheral side wall 4 terminated at its upper end by a convergent wall 5. An inner container made of flexible elastic material 6 containing the composition 7 of active substance and inert vehicle is housed inside the container body, the edge of the inner container being attached to the outer container and a valve-carrying lid 8 being placed on the upper edge of the outer container, on which lid is mounted a flow valve 9 which extends into the outer container via a bent connector 10.

A propellent gas 11 is placed in the free space separating the body of the outer container from the inner container.

The bent connector 10 is connected at its upper end to the entry nozzle 12 and then to the opening 14 of the dispensing device by actuation of the push button 13.

The invention may also be produced using devices comprising a variable-volume pump chamber as described for example in Patent Applications FR-A-2 436 085 and 2 663 909 or as are well known to a person skilled in the art.

Another subject of the invention is a sprayable composition which is intended in particular to be used in a device as has just been described-above and containing in percentage by weight:
75 to 95% of polydiorganosiloxane, in particular of hexamethyldisiloxane,
0.01 to 15% of therapeutic or cosmetic substance,
0 to 10% of agent improving the thixotropy, preferably at least 1%, and
0 to 20% of fillers or additives.

Another subject of the invention is the use of a polydiorganosiloxane as described above as inert vehicle in the devices for dispensing aerosol particles.

Another subject of the invention is a treatment process for the skin, wherein an effective dose of an active substance is applied to an area thereof using a device as described above.

According to one variant, the substance applied is for cosmetic use and is in particular in the form of a powder.

The layer thus deposited unexpectedly exhibits remarkable uniformity and homogeneity which it is not possible to achieve with other inert vehicles.

Moreover, if inert vehicles based on fluorocarbon compounds such as HFA's or CFC's are used, the sprayed material takes the form of a mist whose application cannot be directed as efficiently as when the inert vehicle according to the invention is used.

The invention is now illustrated by an embodiment example which is given as a guide.

The following composition is used:
econazole nitrate 0.2 g
talc 2 g
Aerosil® 200 (colloidal silica) 0.6 g hexamethyldisiloxane marketed by the company Dow Corning under the reference Q7-9179, 17.16 g fragrance 0.04 g The propellent occupying the free space between the two containers is nitrogen. The pressure exerted on the pocket (flexible reservoir) is 8 bar.

The pressurization may also be effected by a mechanical pump.

We claim:

1. A device suitable for dispensing a composition onto the skin in the form of aerosol particles, comprising a container holding the composition, a flow valve extending into said container, and a means of propulsion, wherein the composition comprises, in percentage by weight:

75 to 95% of hexamethyldisiloxane, 0.01 to 15% of an antifungal agent, 0 to 10% of a thixotropic agent, and 0 to 20% of cosmetic additives or densifying fillers.

2. The device as claimed in claim 1, wherein the thixotropic is silica.

3. The device as claimed in claim 1, wherein the antifungal agent is in powder form.

4. The device as claimed in claim 1, wherein the antifungal agent econazole.

5. The device as claimed in claim 1, which is a two-compartment device.

6. The device as claimed in claim 1, which is a variable-volume pump chamber device.

7. The device as claimed in claim 1, wherein the thixotropic agent is present in an amount of at least 1%.

8. The device as claimed in claim 1, wherein the hexamethyldisiloxane has a purity greater than 99.2%.

9. A sprayable composition comprising, in percentage by weight:

75 to 95% of hexamethyldisiloxane, 0.01 to 15% of an antifungal agent, 0 to 10% of a thixotropic agent, and 0 to 20% of filler or additives.

10. The sprayable composition as claimed in claim 9, comprising, in percentage by weight:

80 to 90% of hexamethyldisiloxane, 0.1 to 5% of the antifungal agent, 0 to 10% of the thixotropic agent, and 0 to 20% of fillers or additives.

11. The sprayable composition as claimed in claim 9, wherein the thixotropic agent is present in an amount of at least 1%.

12. The composition as claimed in claim 9, wherein the antifungal agent is econazole.

13. The sprayable composition as claimed in claim 9, wherein the hexamethyldisiloxane has a purity greater than 99.2%.

14. A skin-treatment method comprising spraying on the skin an antifungal-effective amount of the composition as claimed in claim 9.

15. A skin-treatment method comprising spraying on the skin an antifungal-effective amount of the composition as claimed in claim 10.

16. A skin-treatment method comprising spraying on the skin an antifungal-effective amount of the composition as claimed in claim 11.

17. A skin-treatment method comprising spraying on the skin an antifungal-effective amount of the composition as claimed in claim 12.

18. A skin-treatment method comprising spraying on the skin an antifungal-effective amount of the composition as claimed in claim 13.

* * * * *